(12) United States Patent
Waters et al.

(10) Patent No.: US 6,358,221 B1
(45) Date of Patent: Mar. 19, 2002

(54) DISPOSABLE CLEANING APPARATUS FOR PIERCED HUMAN BODY PARTS

(76) Inventors: Joe C. Waters, 4047 Mullikin Rd., Evans, GA (US) 30809; June M. Abernathy, 4515 Saks Rd., Anniston, AL (US) 36206

( * ) Notice: Subject to any disclaimer, the term of this patent is extended or adjusted under 35 U.S.C. 154(b) by 0 days.

(21) Appl. No.: 09/375,491

(22) Filed: Aug. 17, 1999

(51) Int. Cl.[7] .................................................. A61F 9/00
(52) U.S. Cl. .......................................... 604/1; 606/162
(58) Field of Search ........................ 604/1–3; 606/162, 606/188

(56) References Cited

U.S. PATENT DOCUMENTS

| | | | | |
|---|---|---|---|---|
| 3,203,418 A | * | 8/1965 | Johnston ........................ 604/1 |
| 3,500,829 A | * | 3/1970 | Abramowitz .................. 604/1 |
| 4,497,402 A | * | 2/1985 | Karos .......................... 206/210 |
| 4,798,216 A | * | 1/1989 | McCarty et al. ............. 206/210 |
| 5,183,461 A | * | 2/1993 | Hobbs .......................... 604/49 |
| 5,931,845 A | * | 8/1999 | Amyette ..................... 606/162 |
| 6,146,398 A | * | 11/2000 | Satterfield ................... 606/162 |

* cited by examiner

*Primary Examiner*—Dennis Ruhl

(57) ABSTRACT

A disposable kit for achieving and maintaining clean and healthy tissue in body piercing sites on the human body including the eyebrow, chin, nose, mouth, tongue, navel, nipples, and private parts, by cleaning, sterilizing and applying an antiseptic and antibacterial solution. Prevents body piercing complications most often related to the absence of a suitable sterile environment, e.g., using piercing tools or instruments that are not sterile, or the insertion of non-sterile or contaminated appliances, rings, hooks, or whatever device or product is inserted into the pierced cavity. Designed to prevent problems such as irritation, soreness, and closure of the desired pierced opening, which results from contamination, and the absence of a proper sterile and aseptic cleaning kit.

8 Claims, 8 Drawing Sheets

STEP ONE

STEP TWO

STEP THREE

DISPOSABLE CLEANING APPARATUS FOR PIERCED HUMAN BODY PARTS

CROSS-REFERENCE TO RELATED APPLICATIONS

| U.S. PATENT DOCUMENTS | | | |
|---|---|---|---|
| 4,497,402 | 2/1985 | Karos | 206/210 |
| 3,500,829 | 3/1970 | Abramowitz | 604/1 |
| 3,203,418 | 8/1965 | Johnston | 604/1 |
| 5,183,461 | 2/1993 | Hobbs | 604/49 |
| 4,798/216 | 1/1989 | McCarty et al | 206/210 |

STATEMENT REGARDING FEDERALLY SPONSORED RESEARCH OR DEVELOPMENT

Not Applicable

REFERENCE TO MICROFICHE APPENDIX

Not Applicable

BACKGROUND OF THE INVENTION

This invention relates to a disposable kit for cleaning inside the pierced sites or cavities of the human body.

Body piercing has been a long established practice in all countries and cultures. This practice has been manifest in the use of a wide variety of techniques and procedures involving numerous locations on the human body and various sizes of piercing to these sites.

Perhaps the most common and least painful example of body piercing involves piercing of the lower earlobe. Body piercing, however, has become more prevalent and widely accepted among the general population. It has become commonplace for individuals, especially those under twenty years of age in Western Countries, to have body piercing to the eyebrows, chin, lower as well as upper ear ridge, nose, mouth, tongue, navel, nipples, and even more private parts of the body.

Though the practice of body piercing has been around for centuries, people have traditionally experienced some health complications related to this practice. Complications most often are due to the absence of a suitable sterile environment, e.g., using piercing tools or instruments that are not sterile, or the insertion of non-sterile or contaminated appliances, rings, hooks, or whatever device or product is inserted into the pierced cavity, and poor hygiene.

Soreness, bacterial infections and closure of the desired pierced opening result from contamination and the absence of a proper sterile and aseptic cleaning method and kit. Bacterial action results from contamination of sensitive and difficult to get to portions of the body where body piercing has occurred. The removal of foreign matter and particles and the observance of sterile techniques promote more healthy skin tissue and reduce the incidence of infections, irritation, and soreness.

Maintaining clean and healthy tissue in pierced sites is important to one's overall good health. Though there are devices and methods described in prior art that intended and described specifically for cleaning pierced ears, there are no devices, known to the applicants, that have been designed specifically for other body parts, including, but not limited to the eyebrows, chin, nose, mouth, tongue, navel, nipples, and even more private parts of the body. It is to these pierced body sites, which have not been anticipated in prior art, that our invention is addressed.

Other previously patented devices, which have limited application in that they are intended for cleaning the pierced earlobe only and have failed to anticipate cleaning needs of other pierced sites of the human body have been described in the following U.S. Patents: U.S. Pat. No. 4,497,402 of Karos, which claims an apparatus; which uses antiseptic fluid for cleaning and sterilizing ear lobe holes for pierced earrings; Our apparatus is designed for use in numerous pierced sites on the human body using either antiseptic or antibacterial solutions as appropriate since different sites require different solutions. Limitations of the straight firm tip means at one end of the string of Karos' apparatus is overcome in our invention as our insertion tool is "C" shaped and the curvature allows for easier handling, access, and penetration of difficult to reach areas such as the pierced tongue; U.S. Pat. No. 3,500,829 of Abramowitz, which describes an ear hole piercing and treating apparatus, is designed to pierce the lobe of the human ear and substantially eliminate the possibility of infection once the ear has been pierced. It is another object of Abramowitz's apparatus to provide an earring for wearing while allowing for the healing of the ear and for treating sore or infected ears. Unlike Abramowitz's apparatus, our apparatus is not intended for use as an instrument to pierce ears, and is not designed for wearing as a combination piece of jewelry and treatment apparatus, and our apparatus is disposable after each use. Abramowitz's apparatus is kept in the ear and worn over extended periods of time while our apparatus is used for a few moments providing an immediate cleaning with antiseptic or antibacterial solutions, depending on the pierced body part being cleaned, and then discarded. Abramowitz's apparatus has a cleaning surface comprised of metal while our cleaning surface is a textured string; U.S. Pat. No. 3,203,418 of Johnston, which describes and claims an ear swab for use by some individuals is for removing a certain amount of the ear wax from the ears. Johnson's swab has neither application for a pierced earlobe nor any other pierced body site; U.S. Pat. No. 5,183,461 of Hobbs, which describes and claims a method for cleaning a pierced ear hole is comprised of a single length of flexible strand having two ends folded back on itself to form a loop position with the two ends being bonded by being partially melted with heat. Our invention is intended to provide a more durable metal insertion tool whereby the textured string can be more easily inserted into additional pierced body sites; and, U.S. Pat. No. 4,798,216 of McCarty et al, which describes a cleaning method only for pierced ear lobes comprises a thread, such as a floss, being soaked in an astringent and pulled back and forth to clean the ear lobe. Our invention provides an apparatus for cleaning other pierced sites on the human body not anticipated in prior art.

BRIEF SUMMARY OF THE INVENTION

Our invention is a disposable body piercing cleaning kit for cleaning inside pierced sites or cavities on the human body. These sites include, but are not limited to the eyebrows, chin, nose, mouth, tongue, navel, nipples, and even more private parts of the body.

This invention provides a method to deal with soreness, irritation, and closure of the desired pierced openings that result from contamination and the absence of a proper sterile and aseptic cleaning kit. It provides for a kit to remove foreign matter and particles by using a sterile technique, which promotes more healthy skin tissue and reduces the incidence of soreness, irritation, and infections. Such problems are very common and are experienced by individuals from all walks of life all over the world.

This disposable body piercing cleaning kit utilizes newly designed parts in combination with some basic materials and products that are currently available in the marketplace to achieve a uniquely designed and workable invention.

The basic materials utilized in this invention, with all being shown in FIGS. 1, 1A, 2 and 2A, include: a "C" shaped stainless steel insertion tool, with one end having a firm fibrous material or plastic covered end, and the other end having a threading eye FIG. 2(1D) or a sleeved and crimped end FIG. 2B(1D) into which the string is fitted, sealed packages for the insertion tool and textured string FIG. 1A(3,4), three strands of textured cleaning string of various composition, texture, and size; three vials of solution (each approximately 3 ml to 5 ml), one vial containing an antibacterial mouthwash, one vial containing an antiseptic solution, and one vial containing sterile water; three individually prepackaged sterile cleaning and disinfecting alcohol prep pads or other swabs having disinfecting and sterilizing properties; an insertion tool threader for installing the textured cleaning string; a package and storage container base; and, a screw-on cap for the aforementioned devices comprising the disposable body piercing cleaning kit.

BRIEF DESCRIPTION OF SEVERAL VIEWS OF THE DRAWING

FIG. 1A is a perspective view showing a second embodiment of a disposable cleaning apparatus for pierced human body parts which includes an insertion tool with a textured string attached and sealed packages for same. FIG. 2A is a detailed view showing a second embodiment of an insertion tool with a sleeved and crimped end having a textured string attached.

DETAILED DESCRIPTION OF THE INVENTION

Preferred embodiments of the present invention will now be described in greater detail and will be better understood when read in conjunction with the following drawings in which "like parts" bear "like numerals" throughout the several views.

The term "textured cleaning string" as used herein is defined to include, but not be limited to textured string now commercially available being made of cotton, polyester, nylon or other organic or synthetic material having porous and absorbent characteristics.

Figure 1:
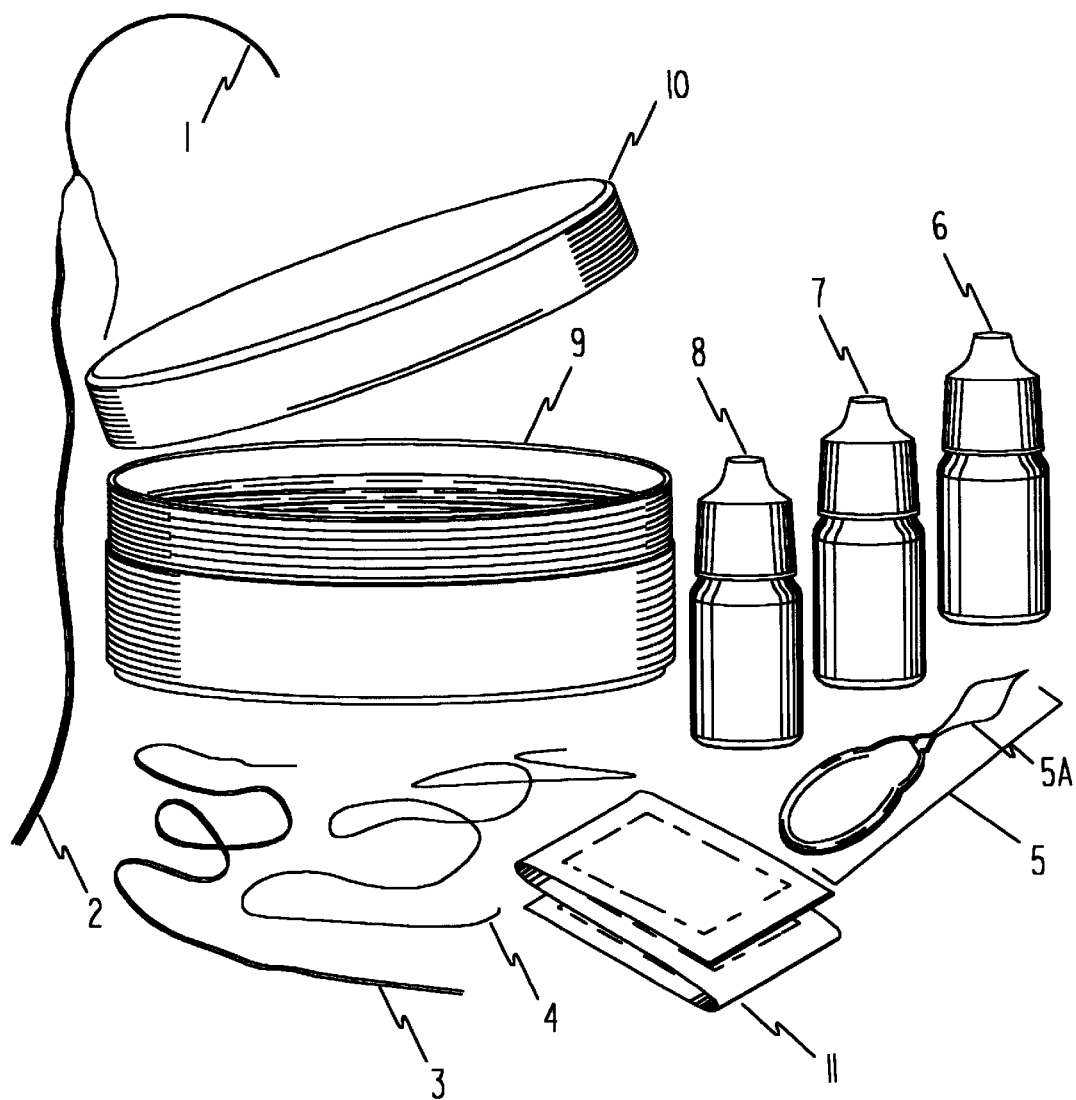
FIG. 1 is a perspective view showing components of the disposable body piercing cleaning kit including: A "C" shaped stainless steel insertion tool 1 pre-threaded with a large size textured cleaning string 2; two extra strands of textured cleaning string, one being medium 3, and one being small 4; a textured cleaning string threader 5 with loop 5A; a 3 ml to 5 ml vial of antibacterial mouthwash 6 for use in cleaning pierced sites within the mouth area, a 3 ml to 5 ml vial of antiseptic solution 7 for use in cleaning other pierced sites, a 3 ml to 5 ml vial of sterilized water 8 for diluting the antibacterial mouthwash 6 and the antiseptic solution 7 as desired; a disposable body piercing cleaning kit container 9 made of plastic, metal or other material used for storing the contents of the disposable body piercing cleaning kit and also serving as a sterilizing reservoir for the insertion tool 1 and cleaning sting 2, 3 and 4 and insertion tool threader 5; a screw-on cap 10 for container 9; and three prepackaged sterile cleaning and disinfecting alcohol prep pads or other swabs 11 having disinfecting and sterilizing properties for cleaning the hands and around the pierced site so as to avoid contamination.

FIG. 1 shows an insertion tool 1 as being a "C" shaped stainless steel tool with one end having a tapered end 1A to allow a firm fibrous material or plastic cover 1B to fit on that end, and allow a smooth contour to the tool. The insertion tool has a rounded end 1C to allow insertion of the insertion tool and textured cleaning string without causing discomfort or injury to the user. On the opposite end of the insertion tool 1 is a threading eye 1D with a large size textured cleaning string 2 pre-attached. FIG. 1A is a perspective view showing a second embodiment of a disposable cleaning apparatus for pierced human body parts which includes an insertion tool 1 with a textured string attached 2 and sealed moisture-proof envelope packages made of aluminum foil or plastic or other material 3 containing the insertion tool and antiseptic or antibacterial solution and the same type packages 4 containing alcohol swabs for cleaning the pierced body site. In this second embodiment, FIG. 2A is a detailed view showing a second embodiment of an insertion tool with one end 1A and 1B being the same insertion tool as described in FIG. 1 with the other end 1D and 1E being a sleeved and crimped end with a textured string 2 attached.

Also shown in FIG. 1 are two extra strands of textured cleaning string 3 and 4; a textured cleaning string threader 5 with a loop 5A; a 3 ml to 5 ml vial of antibacterial mouthwash 6 for use in the mouth area, a 3 ml to 5 ml vial of antiseptic solution cleaning 7 for cleaning external piercing sites; a 3 ml to 5 ml vial of sterilized water 8 to dilute 6 and 7 as desired; a disposable body piercing cleaning kit container 9 made of plastic, metal or other material for storing the contents of the disposable body piercing cleaning kit also serving as a sterilizing reservoir for the insertion tool 1 and cleaning stings 2, 3 and 4; a screw-on cap 10 for container 9; and three prepackaged sterile cleaning and disinfecting alcohol prep pads or other swabs having disinfecting and sterilizing properties 11 for cleaning the hands and around the pierced site to avoid contamination.

After opening the container and removing the contents of the disposable body piercing cleaning kit FIG. 1, the hands and piercing site are cleansed using the prepackaged sterile cleaning and disinfecting alcohol prep pads or other swabs 11. The pre-threaded cleaning string 2 is selected or cleaning string 3 or 4 is threaded following the illustration in FIG. 12. The insertion tool 1 and threaded cleaning string is then placed in container 9 upon which the contents of either Vial 6 or 7 is poured, depending on the location of the piercing site being cleaned. The insertion tool 1 with the attached threaded textured cleaning string 2, 3 or 4 should be fully immersed and saturated with the antibacterial mouthwash or antiseptic solution before being removed and used as illustrated in FIGS. 6, 7, 8, 9, 10 and 11. Textured cleaning strings 2, 3 and 4 may be used only one time and must be discarded along with other used articles in the kit. The insertion tool 1 and textured cleaning string threader 5 are reusable, and the antibacterial mouthwash 6, antiseptic solution 7, and sterile water 8 may be used until depleted.

Figure 2:
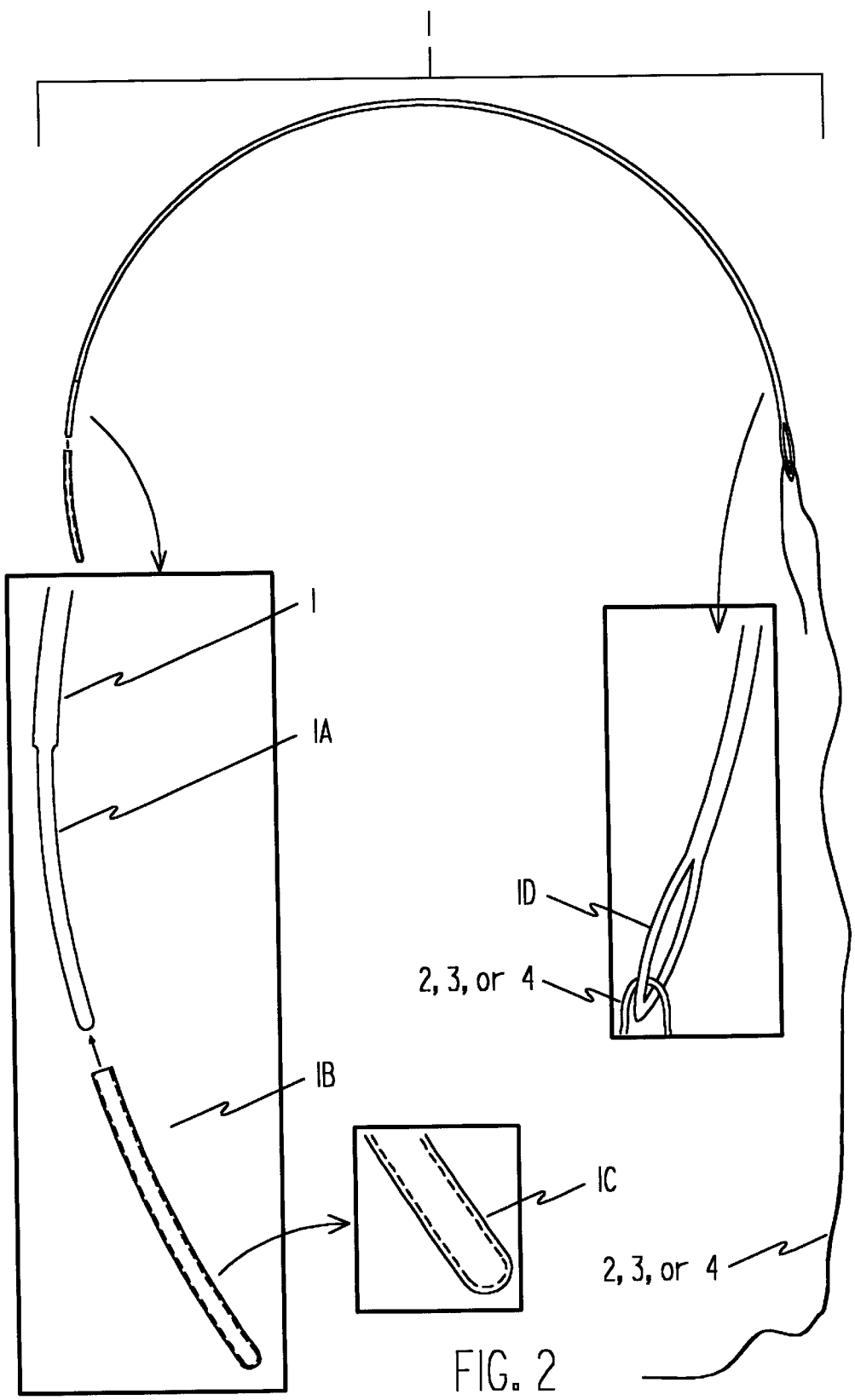
FIG. 2 is a detail view of the "C" shaped stainless steel insertion tool 1 with exploded details of the one end being covered with Teflon or plastic 1B and how it fits on the tapered end 1A of the "C" shaped stainless steel insertion tool 1 and a detail of the Teflon or plastic covered end showing the rounded end 1C that inserts into the pierced area of the body; the other end of the insertion tool 1 having an threading eye 1D being shown in detail with an attached textured cleaning string 2, 3 or 4.

FIG. 2 shows a textured cleaning string 2, 3 or 4 threaded through the eye 1D of the "C" shaped stainless steel insertion tool 1. The insertion tool's 1 tapered end 1A is covered with a firm fibrous material, plastic or other material 1B and rounded 1C on the end to assure a gentle and smooth entry through the pierced site.

Figure 3:
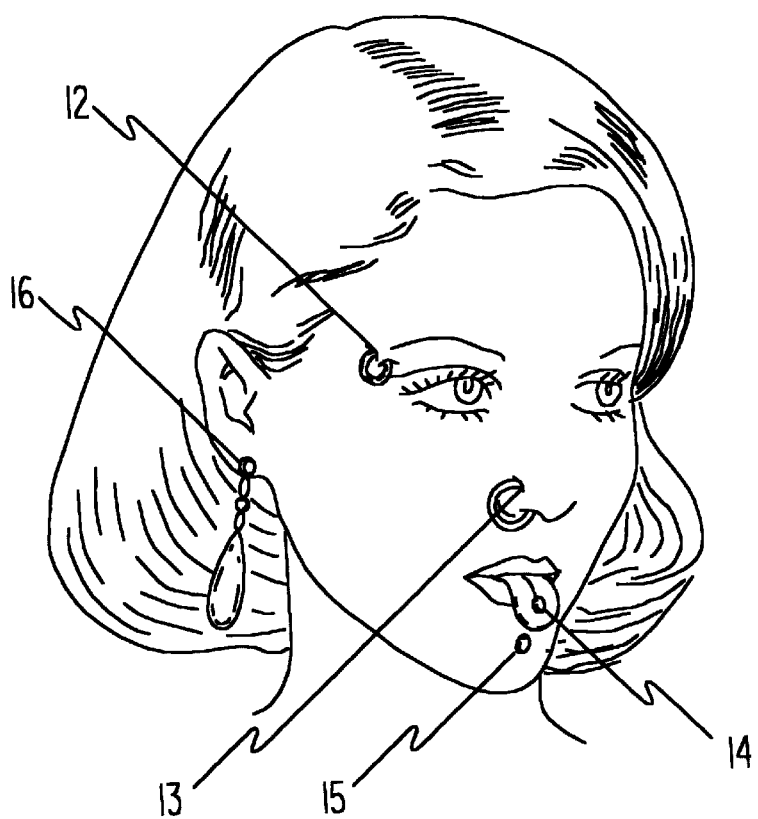
FIG. 3 is a perspective view showing the general location of common body piercing sites being the eyebrows 12, nostrils 13, tongue 14, chin area 15, earlobes 16, and the navel 17. There are, of course, other areas of the body that are pierced, which are not illustrated.
Figure 3:
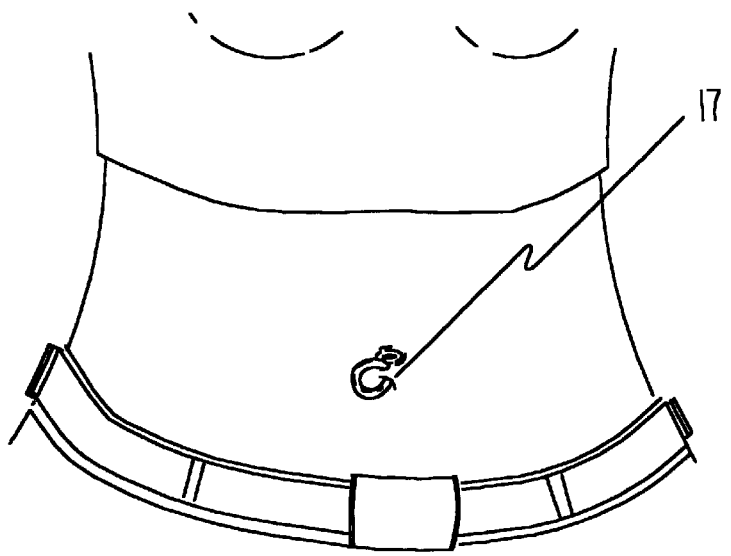

FIG. 3 shows the general locations of common body piercing sites being the eyebrows 12, nostrils 13, tongue 14, chin area 15, earlobes 16, and the navel 17. There are, of course, other areas of the body that are pierced, which are not illustrated. The disposable body piercing cleaning kit is designed for use in all body piercing sites.

Figure 4:
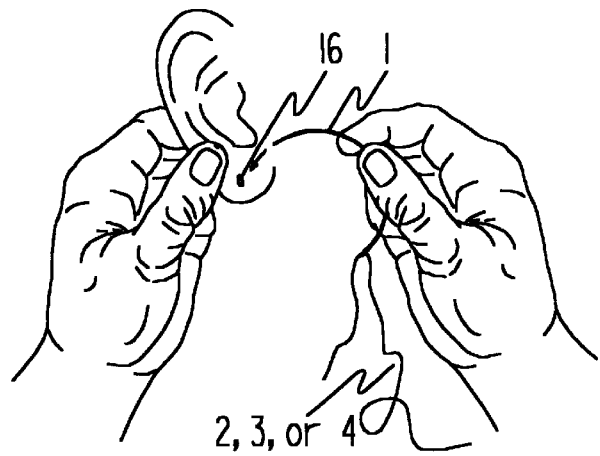
FIG. 4 is a perspective view showing the Teflon or plastic covered end of the "C" shaped stainless steel insertion tool 1 with the attached textured cleaning string 2, 3 or 4 on the opposite end ready to be inserted into the pierced area of the earlobe 16.
Figure 5:
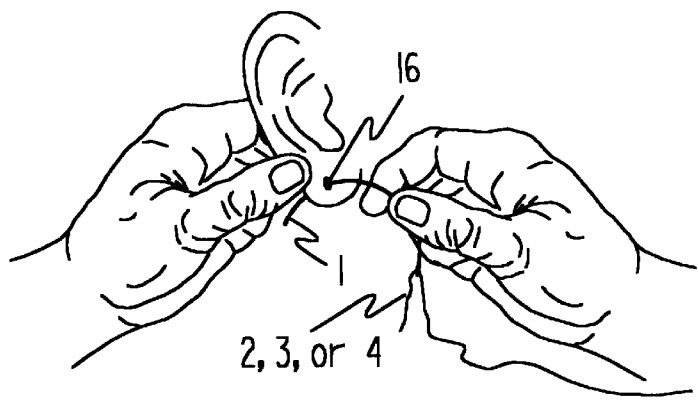
FIG. 5 is a perspective view showing the "C" shaped stainless steel insertion tool 1 with the attached textured cleaning string 2, 3 or 4 inserted through the pierced area of the earlobe 16.

FIG. 4 shows the "C" shaped stainless steel insertion tool 1 with the attached textured cleaning string 2, 3 or 4 on the opposite end ready to be inserted into the pierced area of the earlobe 16. The insertion is made gently following the contour of the pierced site.

FIGS. 5, 7, 8, 9, 10, and 11 show the "C" shaped stainless steel insertion tool 1 being gently pulled through the pierced opening 12, 13, 14, 15, 16 and 17 with the insertion tool 1 being separated from the textured cleaning string 2, 3 or 4 immediately after insertion of the textured cleaning string 2, 3 or 4 through the pierced opening 12, 13, 14, 15, 16, or 17.

Figure 6:
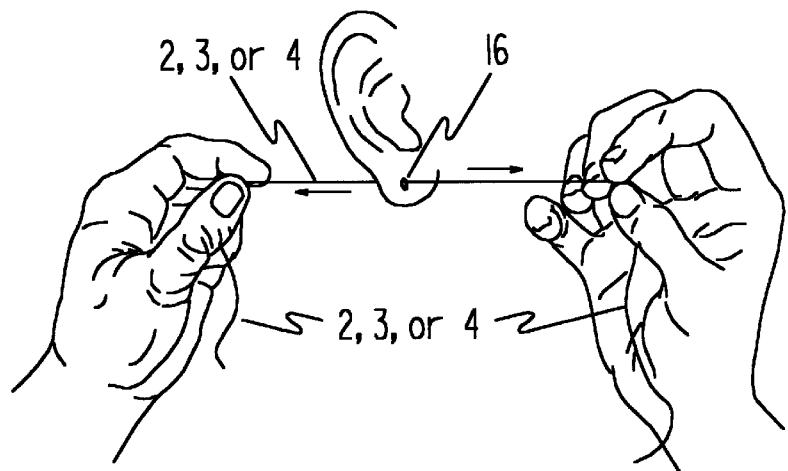
FIG. 6 is a perspective view showing the earlobe 16 with the "C" shaped stainless steel insertion tool removed and the textured cleaning string 2, 3 or 4 being gently pulled back and forth to clean the pierced area of the earlobe 16.
Figure 7:
FIG. 7 is a perspective view showing the "C" shaped stainless steel insertion tool 1 with the attached textured cleaning string 2, 3 or 4 inserted through the pierced area of the eyebrow 12. Cleaning of the pierced area is accomplished as illustrated in FIG. 6.
Figure 8:
FIG. 8 is a perspective view showing the "C" shaped stainless steel insertion tool 1 with the attached textured cleaning string 2, 3 or 4 inserted through the pierced area of the nostril 13. Cleaning of the pierced area is accomplished as shown in FIG. 6.
Figure 9:
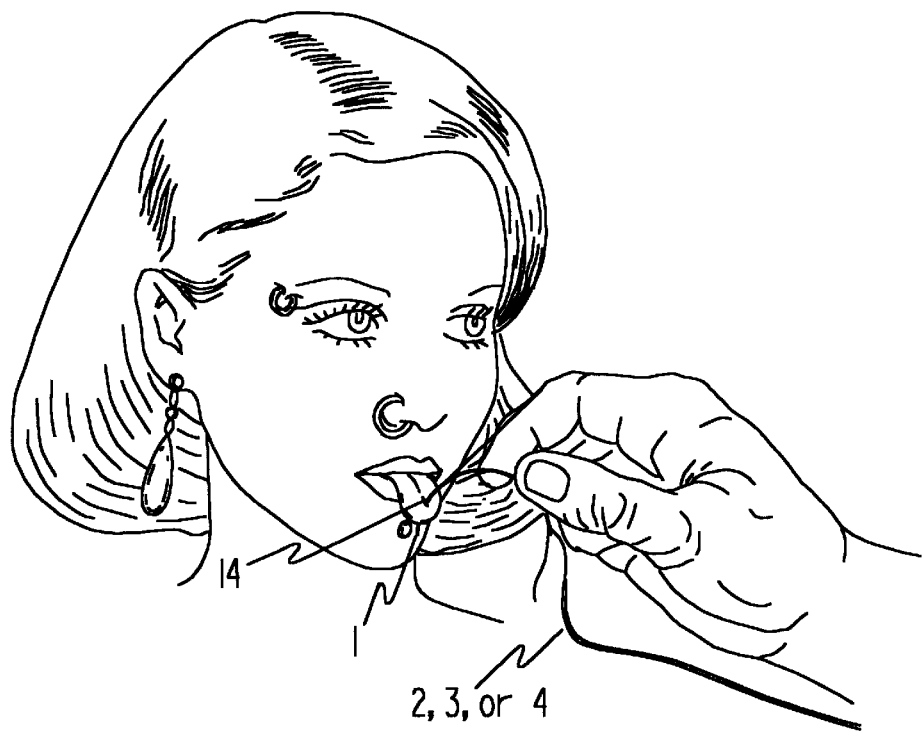
FIG. 9 is a perspective view showing the "C" shaped stainless steel insertion tool 1 with the attached textured cleaning string 2, 3 or 4 inserted through the pierced area of the tongue 14. Cleaning of the pierced area is accomplished as illustrated in FIG. 6.
Figure 10:
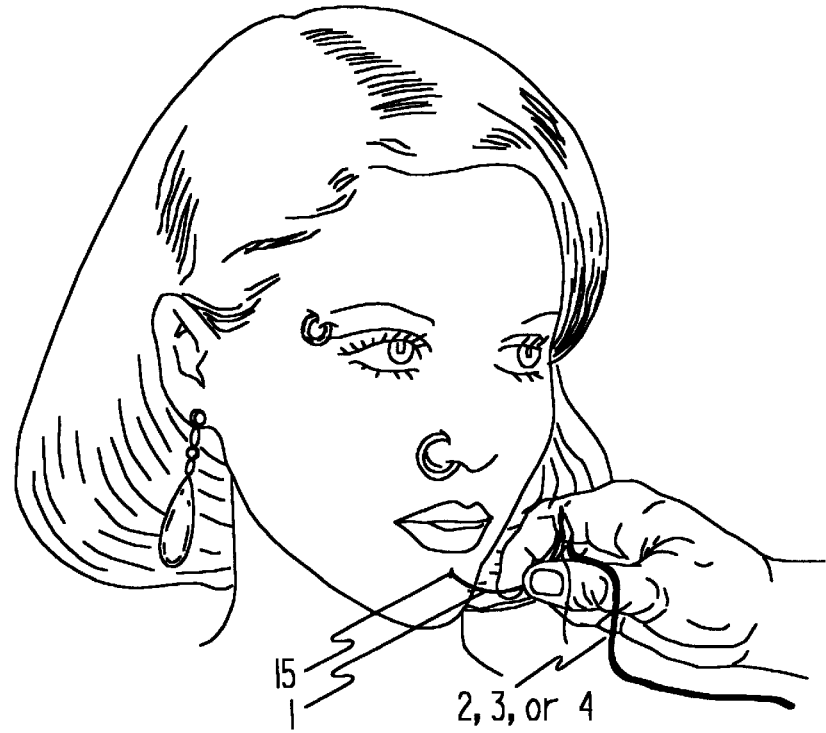
FIG. 10 is a perspective view showing the "C" shaped stainless steel insertion tool 1 with the attached textured cleaning string 2, 3 or 4 inserted through the pierced area of the chin 15. Cleaning of the pierced area is accomplished as illustrated in FIG. 6.
Figure 11:
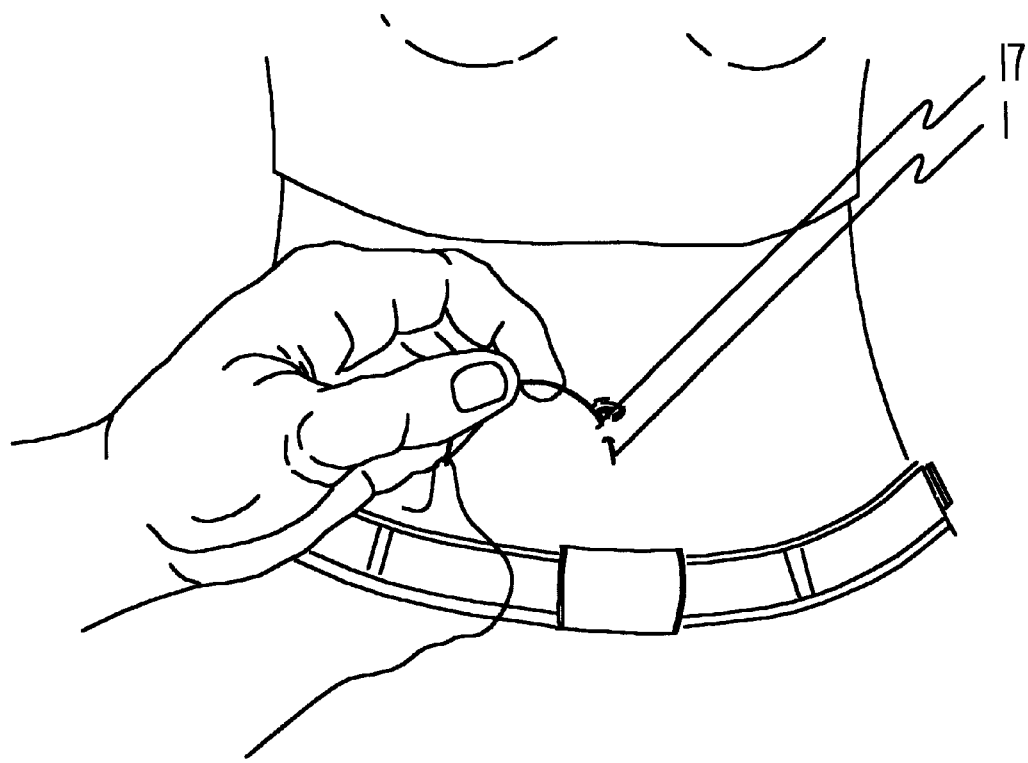
FIG. 11 is a perspective view showing the "C" shaped stainless steel insertion tool 1 with the attached textured cleaning string 2, 3 or 4 inserted through the pierced area of the Navel 16. Cleaning of the pierced area is accomplished as illustrated in FIG. 6.

FIG. 6 shows the textured cleaning string 2, 3 or 4 being gently pulled back and forth a few times with short strokes to clean the inside of the pierced area with cleaning being completed when the textured cleaning string is pulled through the pierced area in the same direction it was initially threaded.

Figure 12:
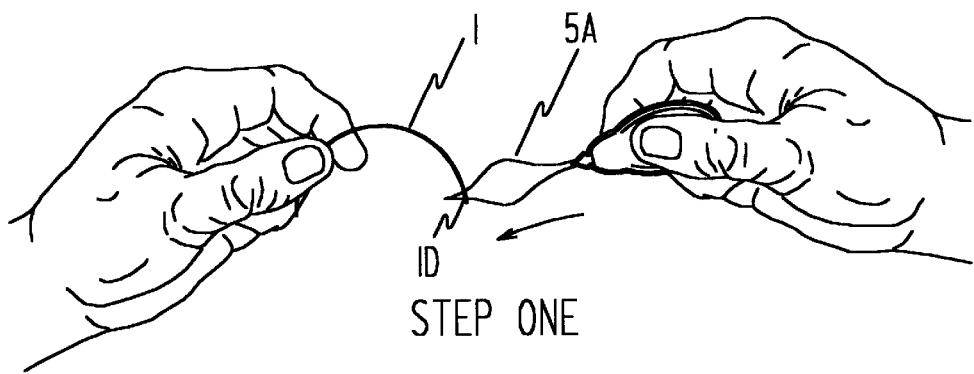
FIG. 12 is a perspective view showing how the textured cleaning string 2, 3 and 4 is threaded through the "C" shaped stainless steel insertion tool 1 using the threader 5.
Figure 12:
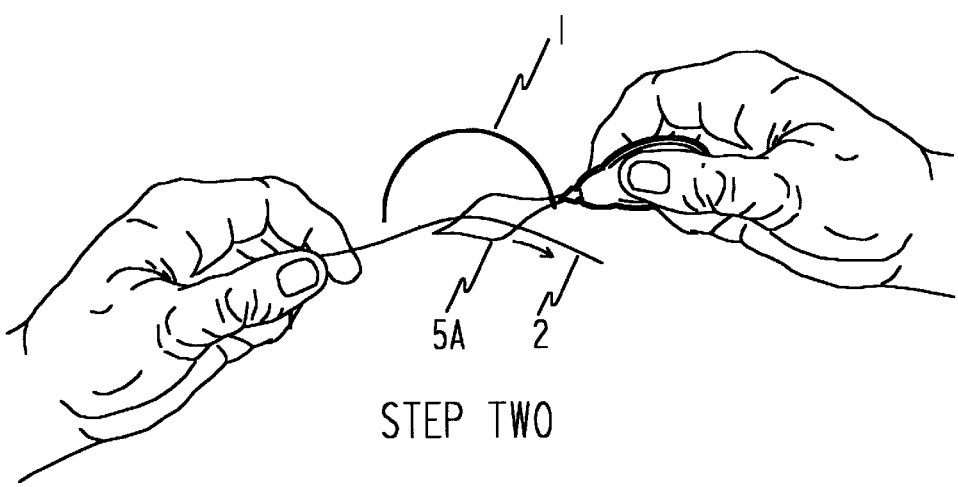
Figure 12:
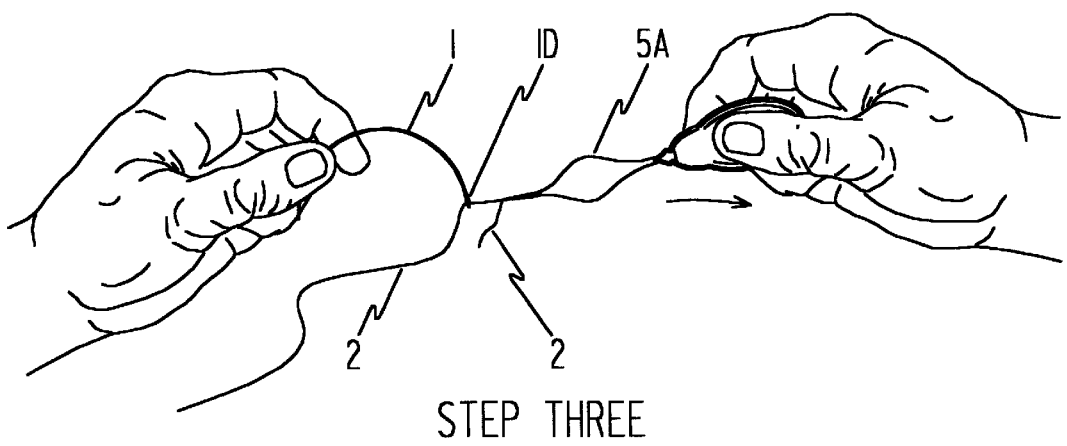

FIG. 12 shows how textured cleaning string 2, 3 and 4 is threaded through the "C" shaped stainless steel insertion tool 1 using the threader 5 illustrating:

Step one—the textured cleaning string threader 5 with the loop end 5A being inserted into the eye of the "C" shaped stainless steel insertion tool 1D;

Step two—an end of the textured cleaning string 2, 3 or 4 being inserted through the loop end 5A of the threader 5; and, Step three—the loop 5A being pulled through the eye of the "C" shaped stainless steel insertion tool 1D to complete the threading of the textured cleaning string 2, 3 or 4.

What we claim as our invention is:

1. A disposable body piercing cleaning kit for cleaning inside human body piercing sites including the eyebrows, chin, nose, mouth, tongue, navel, nipples, and private parts which comprises:

an insertion tool;

textured cleaning strings;

cleaning and disinfecting alcohol prep pads;

antiseptic solution;

antibacterial solution;

sterile water;

3 ml to 5 ml plastic vials;

sewing needle threader;

a packaging and storage container.

2. A cleaning kit as defined in claim 1, wherein said insertion tool is "C" shaped and has on one end a needle shaped eye, with an opposite end of the insertion tool comprising a round end.

3. A cleaning kit as defined in claim 1, wherein the round end of said "C" shaped insertion tool described comprises a plastic material covering the round end.

4. A cleaning kit as defined in claim 1, wherein said textured cleaning strings are made of cotton.

5. A cleaning kit as defined in claim 1, wherein said textured cleaning strings are made of polyester.

6. A cleaning kit as defined in claim 1, wherein said textured cleaning strings are made of nylon.

7. A cleaning kit as defined in claim 1, wherein said sewing needle threader comprises hand held sewing needle threader.

8. A cleaning kit as defined in claim 1, wherein said packaging and storage container comprises a container having a screw-on lid.

* * * * *